(12) United States Patent
Perthu

(10) Patent No.: US 6,595,962 B1
(45) Date of Patent: Jul. 22, 2003

(54) INJECTION DEVICE

(75) Inventor: Michael Perthu, Copenhagen (DK)

(73) Assignee: Union Medico, Copenhagen (DK)

( * ) Notice: Subject to any disclaimer, the term of this patent is extended or adjusted under 35 U.S.C. 154(b) by 0 days.

(21) Appl. No.: 09/890,953

(22) PCT Filed: Dec. 8, 1999

(86) PCT No.: PCT/DK99/00690
§ 371 (c)(1),
(2), (4) Date: Sep. 18, 2001

(87) PCT Pub. No.: WO01/41837
PCT Pub. Date: Jun. 14, 2001

(51) Int. Cl.$^7$ ................................................ A61M 5/00
(52) U.S. Cl. ......................... 604/187; 604/157; 604/181
(58) Field of Search ............................... 604/131, 134, 604/136–138, 156, 157, 181, 117, 116, 144.12, 174, 187; 606/172

(56) References Cited

U.S. PATENT DOCUMENTS

| | | | |
|---|---|---|---|
| 938,597 A | * 11/1909 | Lombardo | 604/157 |
| 2,295,849 A | * 9/1942 | Kayden | 604/136 |
| 3,605,742 A | 9/1971 | Tibbs | |
| 3,702,608 A | * 11/1972 | Tibbs | 128/218 F |
| 3,941,130 A | 3/1976 | Tibbs | |
| 4,026,288 A | 5/1977 | Costa et al. | |
| 4,040,419 A | * 8/1977 | Goldman | 128/215 |
| 4,333,459 A | 6/1982 | Becker | |
| 4,520,815 A | * 6/1985 | Marinoff | 128/303 R |
| 4,680,011 A | 7/1987 | Boinot | |

FOREIGN PATENT DOCUMENTS

| | | |
|---|---|---|
| DE | 3322 923 | 1/1985 |
| NO | 86184 | 7/1955 |
| WO | WO 97/20588 | 6/1997 |

* cited by examiner

*Primary Examiner*—Brian L. Casler
*Assistant Examiner*—Jennifer Maynard
(74) *Attorney, Agent, or Firm*—Venable LLP; John P. Shannon; Chad C. Anderson

(57) ABSTRACT

An injection device (1) has a slide (3) which can be displaced in relation to a housing (2) from a retracted position to an injection position, and which comprises a portion (8) situated within the housing (2) and a portion (6) situated outside the housing, both portions (6, 8) being interconnected through a groove (10) in the housing (2). The portion (6) situated outside the housing (2) has a syringe holder (5) for securing a hypodermic syringe (4), and the slide (3) is pretensioned toward the injection position. The housing (2) at the groove (10) is constituted by a tube part, the outer and/or inner surface (7, 9) of which forms a guide for the slide (3), and the slide (3) has one or more contact faces which are in contact with the guide at least at three areas distributed over more than the half of the circumference of the tube part.

13 Claims, 4 Drawing Sheets

Figure 1:
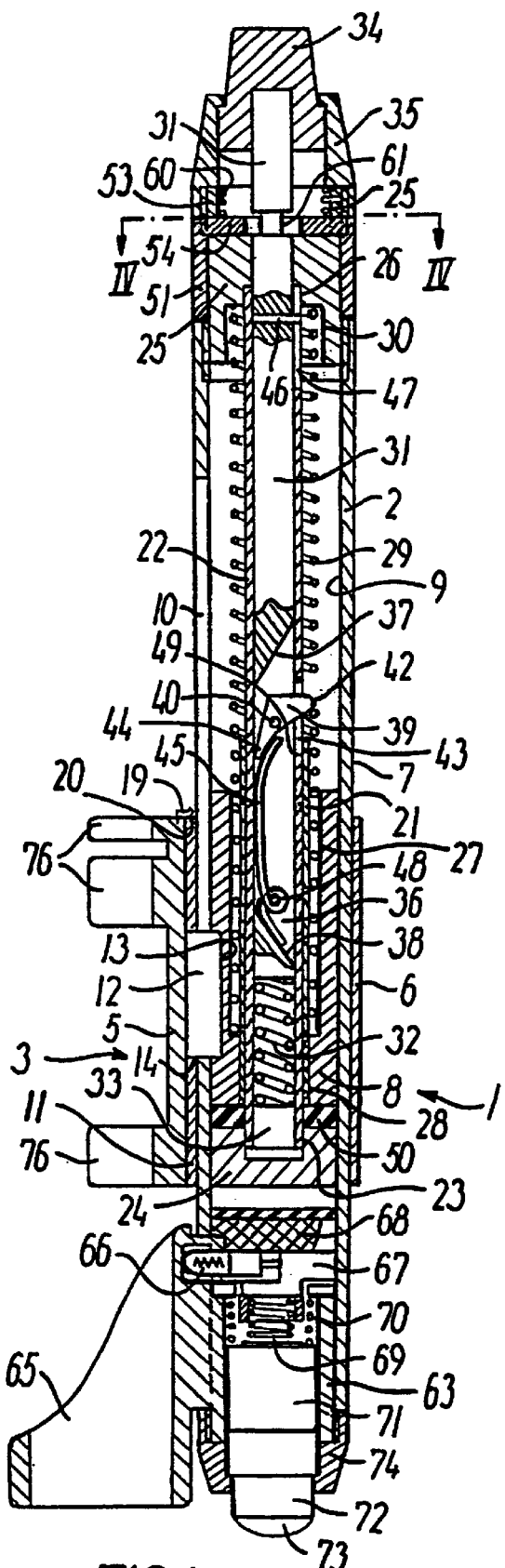

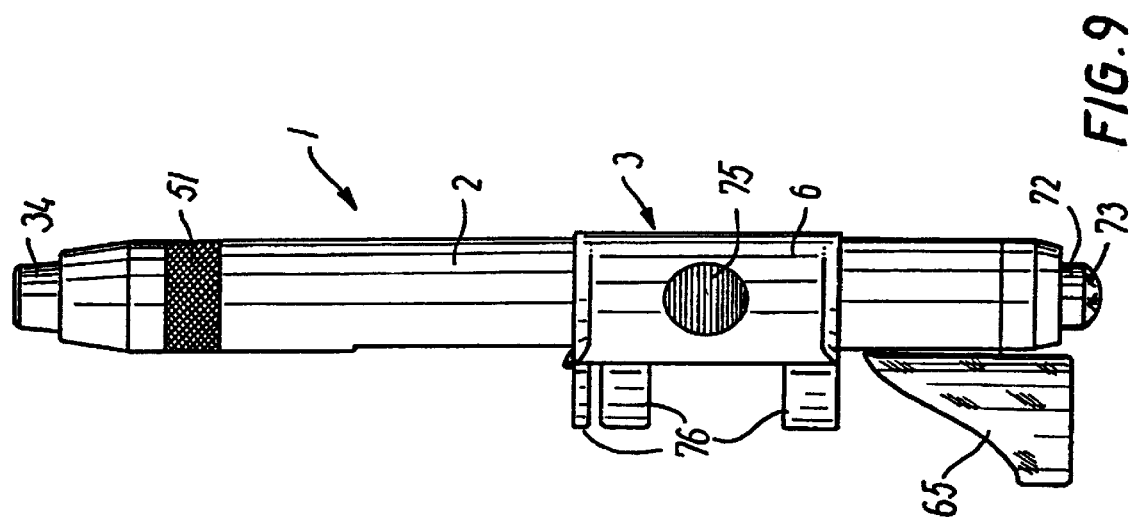
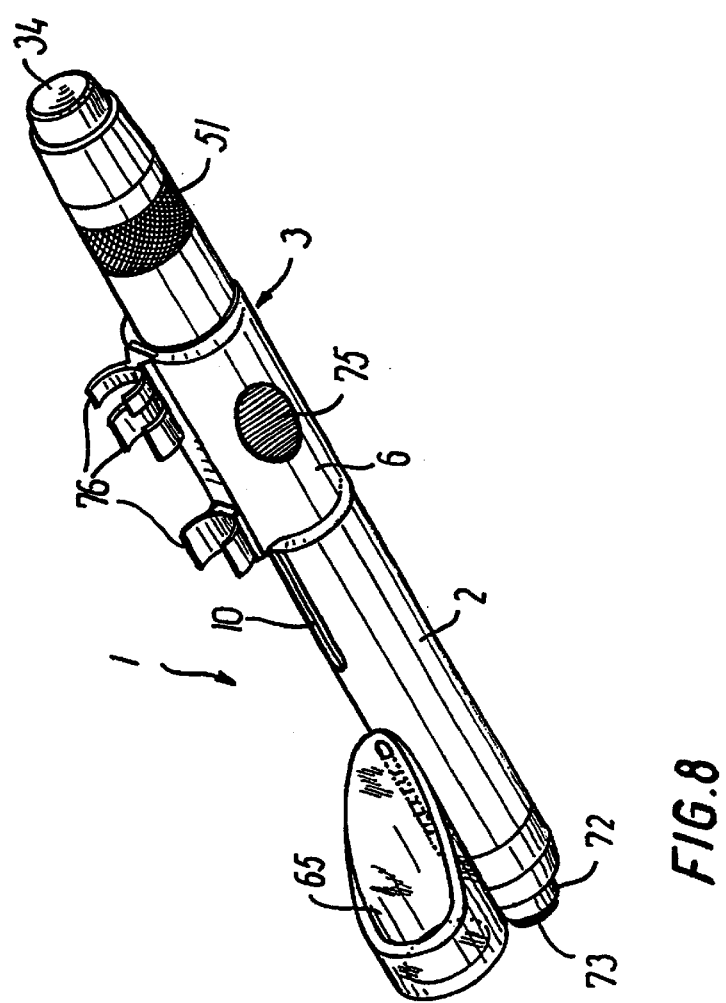

INJECTION DEVICE

The present invention relates to an injection device with a slide which can be displaced in relation to a housing from a retracted position to an injection position, where the slide comprises a portion situated within the housing and a portion situated outside the housing, both portions being interconnected through a groove in the housing, where the portion situated outside the housing has a syringe holder for securing of a hypodermic syringe, and where the slide is pretensioned toward the injection position by a spring situated in the housing.

NO 86184 discloses an apparatus for operation of a hypodermic syringe. A syringe holder is displaceable along a guide extending along one side of a box-shaped housing which may be opened by removal of a cover extending in the entire longitudinal direction of the housing. At the guide side of the housing, there is within the latter arranged a tension spring which is tensioned by displacement of the syringe holder to the retracted position of the holder. In the retracted position, the syringe holder is retained by a beak which is fastened rotatably to the housing and which can be released from the holder by means of a guide rod extending in the housing opposite the guide side.

U.S. Pat. No. 3,605,742 discloses an injection device with a box-shaped housing in which an internal syringe holder may be displaced in its longitudinal direction. A hypodermic syringe can be inserted in a recess in the syringe holder, a longitudinal wicket in one side of the housing having to be opened beforehand such that the syringe can pass-through an opening in the wall of the housing. The syringe holder can then be displaced to its retracted position by operation of a handle projecting through the side of the housing. By this displacement, two tension springs fastened at the bottom of the housing and at the upper end of the syringe holder, respectively, and extending each in separate longitudinal recesses in the syringe holder, are tensioned.

U.S. Pat. No. 4,333,459 discloses an injection device with a pistol-shaped housing, along the elongated top side of which a syringe holder can be displaced. The syringe holder has an H-shaped cross section where the bottom legs of the H are constituted by sheets each with its longitudinal groove guided over two guide bolts, the bolts projecting from the sides of the housing. By displacement of the holder to its retracted position, is a tension spring arranged under the holder and between the upright side walls of the housing is tensioned. The syringe holder can be released from the retracted position by operation of a pistol grip.

U.S. Pat. No. 4,026,288 discloses further a pistol-shaped injection device where the syringe holder is guided on a bar-shaped guide. A spring is arranged around the guide for propulsion of the holder in order to inject the needle of the syringe in a skin area. By displacement of the syringe holder, a gearwheel is rotated via a rack on the holder, and a pistol grip blocks in its passive position this gearwheel such that the holder is secured. By operation of the grip, the holder is released.

The object of the present invention is to provide an injection device simple as to construction and with a more stable function than the known devices.

For this purpose, the device according to the invention is characterized in that the housing at the groove is constituted by a tube part, the outer and/or inner surface of which forms a guide for the slide, and that the slide has one or more contact faces which are in contact with the guide at least at three areas distributed over more than the half of the circumference of the tube part.

By the fact that the housing itself acts as a tubular guide for the slide, a circumferential face of the guide can be obtained with a larger circumference than if the guide is a separate element within the housing, and thus a more rigid guide is obtained, and by letting at the same time the slide glide on the guide at at least three areas distributed over more than the half of the circumference of the tube part, the slide is retained on the guide in an exact and stable guidance. The rigid guide and the exact guidance result together in an extremely reliable performance. A tubular housing is moreover very simple to produce.

In an advantageous embodiment, the slide portion situated outside the housing encircles the tube part along the entire circumference of the tube part. Thus, an even more stable guidance is obtained as the slide can have contact points in touch with the guide around the complete circumference of the guide, either a continuous face or discrete faces, and as the slide in itself can be more rigid because of the tubular form. Furthermore, the slide arranged around the housing forms a stable and an easy accessible finger grip for operation of the slide by retraction of this for tensioning of the spring.

The outside diameter of the tube part can advantageously be at least 8 mm, and preferably at least 12 mm, a more secure grip around both the housing of the injection device and the slide being thus obtained. Furthermore, as a consequence of additional thickness of material, the total weight of the device can preferably be at least 40 g, and further preferably at least 60 g, the total inertia of the device thus assuring a more steady handling of the device at the operation, and thus a more exact and stable injection.

In an embodiment, an elongated release mechanism extends coaxially with the tube part in the housing and carries a pawl which is spring-loaded to engage with and retain the slide in the retracted position of the slide, the release mechanism can at a first end of the housing cooperate with a release button such that when actuating the release button, the pawl can be disengaged from the slide, and the pre-tensioning spring of the slide is arranged around the release mechanism. In this way, a substantially rotationally symmetrical structure of the device is made possible, which simplifies both the production of the required components and their mounting. It is further possible to use one single spring which is strong enough for the pretensioning of the slide, as the spring can have an outside diameter which is merely a little smaller than the inside diameter of the housing. It is also an advantage that the release button can be placed at one end of the housing as this provides an easy operation, e.g. the button can be designed for axial displacement in the housing at the release.

In an embodiment simple as to production, the release mechanism comprises a release tube with a rod which can be displaced axially in the tube, and the pawl is pivotally journalled in a recess in the rod and has an end which can project through a slit in the release tube, and which at displacement of the rod can be swung into the tube. Thus, also the mounting is facilitated as the release mechanism can be assembled separately and then guided into the housing from the end of the housing.

The portion of the slide situated within the housing can encircle the release mechanism which facilitates the mounting further as the release mechanism can be guided into the housing and through the slide with the slit for the pawl facing an arbitrary direction since the pawl can thus enter into engagement with the slide in any angle position of the release tube in relation to the slide. The portion of the slide situated within the housing can further preferably close the cavity between the release mechanism and the internal surface of the tube part. Thus, at the end of the movement of the slide at injection, an overpressure of air can be created under the slide, whereby a soft braking of the movement of the slide is obtained.

In another embodiment, the release mechanism is provided with a locking mechanism which is spring loaded for locking the pawl in the engagement position of the pawl with the slide and which can release the pawl for releasing by operation of a lock button. This assures the slide not being released unintentionally before the injection device is placed above the skin area where the injection is to be made. The locking mechanism being spring loaded for locking the pawl, the locking is effected automatically by return of the slide without any further operation of the locking mechanism. Before the injection can be made, the lock button has thus to be actuated and it further has to be pressed against the spring load during the release itself of the slide. It is thus prevented that the actuation of the lock is forgotten or that the lock is brought out of function by mistake.

In a particularly easy-to-operate and simple embodiment, the rod, of the release mechanism has a circumferential groove with which a lever can engage when the rod is in its inactivated position where the pawl can engage with the.slide, and the lock button is designed as a lock ring which when turned coaxially about the rod can lift the lever out of engagement with the groove. By designing the lock button as a lock ring, the button can first be turned by means of two fingers and then retained by these two fingers and at the same time the fingers retain the housing itself, the fingers being able to seize both the ring and the housing. The lock ring can preferably be situated at the release button as both the lock ring and the release button in this way can be operated by the fingers of the same hand. The other hand is thus free possibly to control the other end of the device at the skin area where the injection is to be made.

The syringe holder can be detachably fastened on the slide whereby different holders fitting different types of injection syringes can be used. The holder can preferably be designed to be fastened by insertion in a key slot where it is retained by a resilient bow in engagement with the slide so that it can be detached form the slide by pressing back the bow.

In a particularly practical embodiment, the housing has at its other end a lamp which can be lit by actuation of an axially projecting push button. When placing the injection device at a skin area, the push button can thus be activated automatically, as the end of the device with the projecting button is pressed against the skin area whereby the skin area can be illuminated by the lamp for inspection of the area, e.g. a vein can be made visible. Furthermore, the lamp can transilluminate a hypodermic syringe mounted on the holder when the latter is in the injection position. It can thus be detected if any blood can be drawn back in the syringe which indicates that a vein has been hit.

The housing can moreover at its other end have a bow which can be pressed against and extend a skin surface where an injection is to be made. The bow can preferably be made of light transmitting material, such as limpid plastic, and can be adapted such that it can be illuminated by the lamp. The bow can thus guide the light toward the skin area to be inspected.

Figure 2:
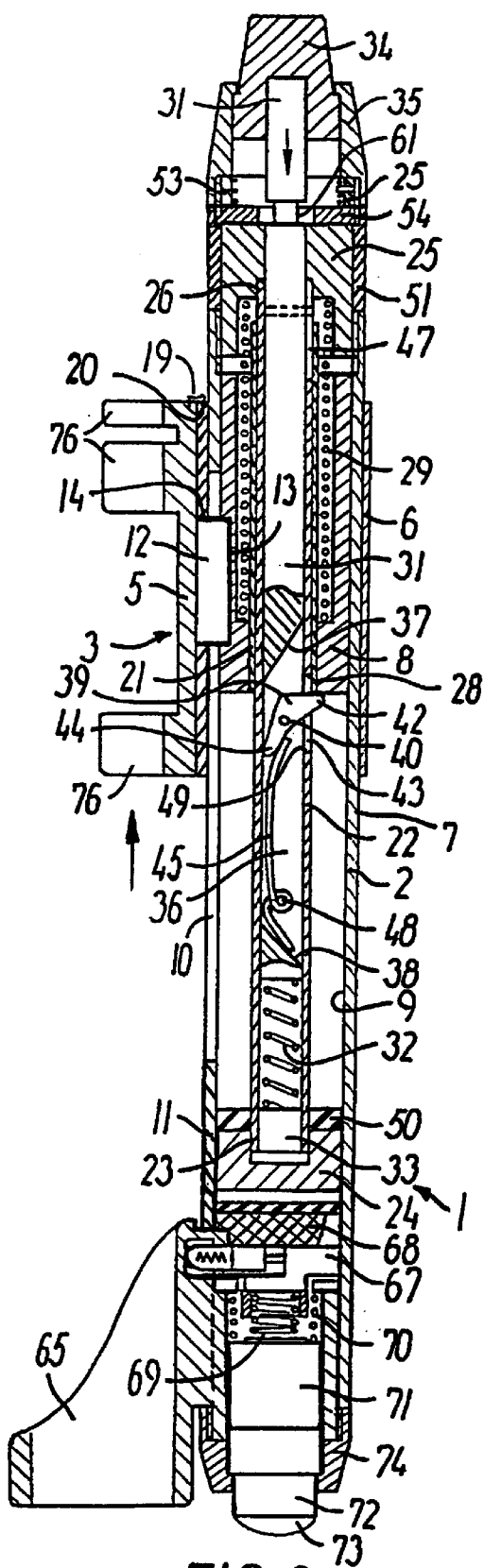
Figure 3:
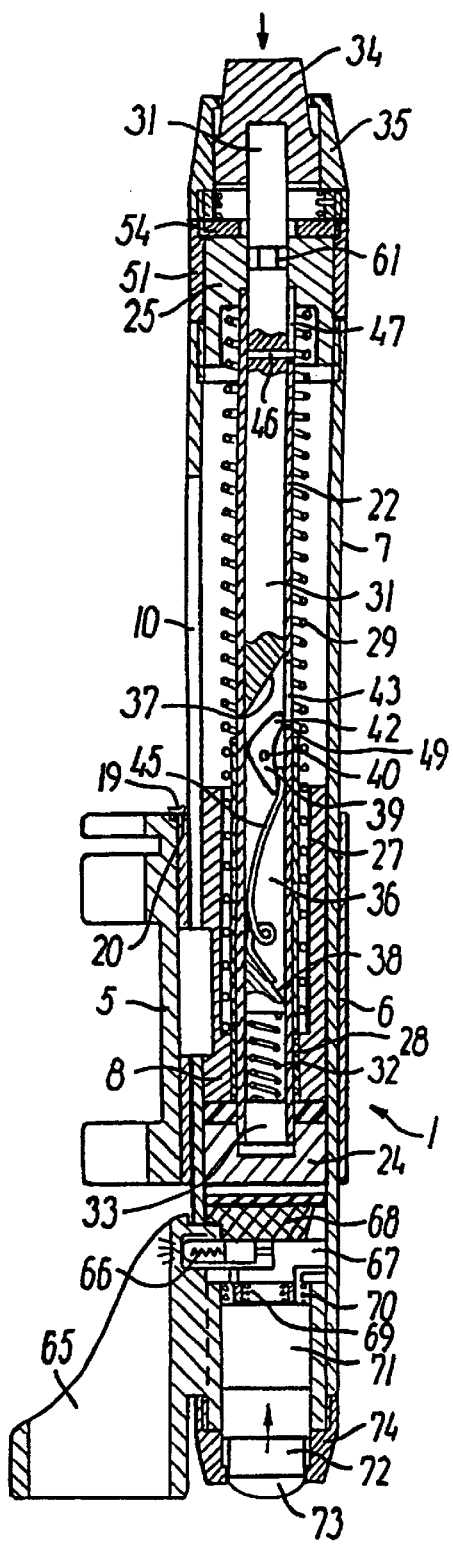
Figure 6:
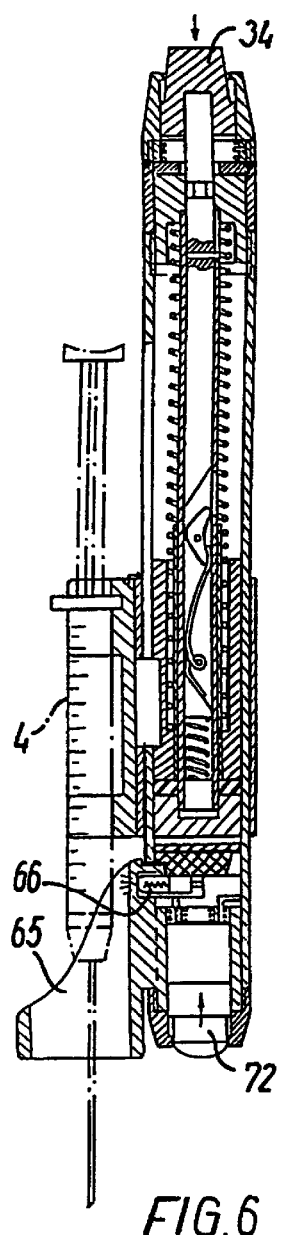
Figure 4:
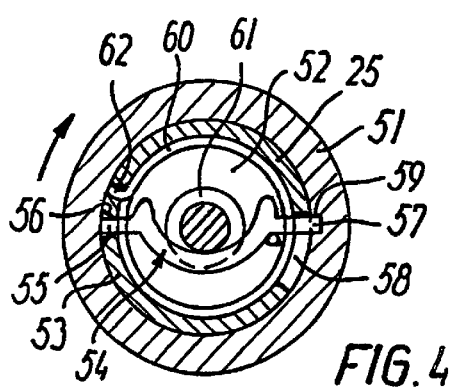
Figure 7:
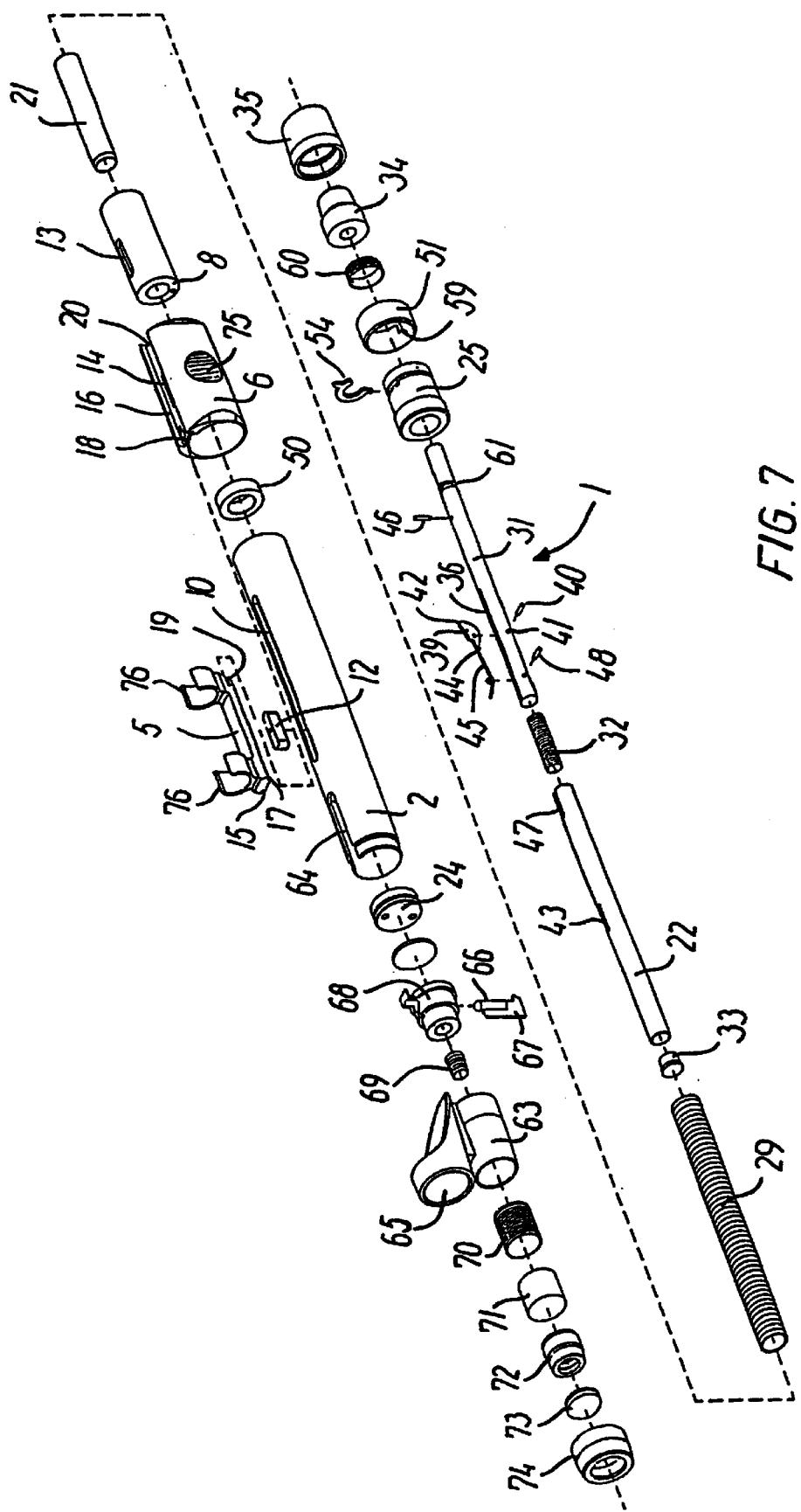

The invention will in the following be explained more in detail by means of examples of embodiments with reference to the schematic drawing, in which FIG. 1 shows an injection device according to the invention, seen in an axial section where the slide is in its unloaded initial position, FIG. 2 the injection device in FIG. 1 where the slide is locked in the retracted position, FIG. 3 the injection device in FIG. 1 where the push button is activated, and the slide is in the injection position, FIG. 4 an enlarged cross section through the device along the line IV—IV in FIG. 1, FIG. 5 the injection device in FIG. 1 with a mounted hypodermic syringe where the slide is locked in the retracted position, FIG. 6 the injection device in FIG. 1 with a mounted hypodermic syringe where the slide is in the injection position, FIG. 7 is an exploded view of the injection device in FIG. 1, FIG. 8 a perspective view of the injection device in FIG. 1, and FIG. 9 a side view of the injection device in FIG. 1.

Figure 5:
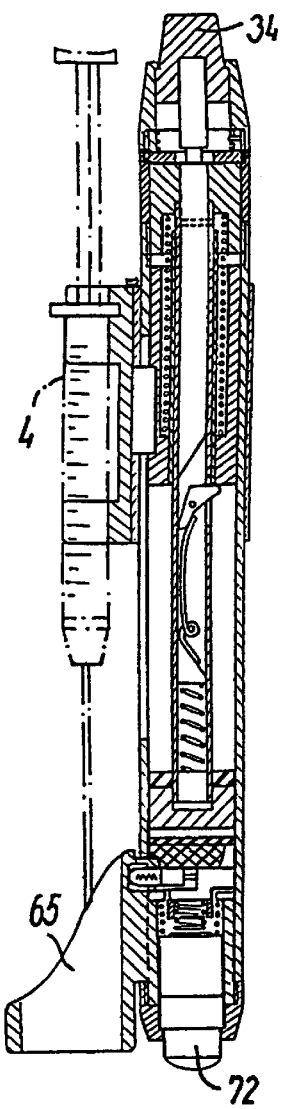

FIG. 1 shows an injection device 1 with a tubular housing 2 which forms a guide for a slide 3 on which a hypodermic syringe 4 can be mounted by means of a syringe holder 5, as shown in FIGS. 5 and 6. The injection device 1 can be used to guide a hypodermic syringe, in particular by intramuscular injections, as the needle by such injections is especially long and thus unpleasant to enter manually. In the following, reference will be made to the device 1 in the position shown in FIG. 1, however, during use, it may be oriented arbitrarily.

The slide 3 comprises a tubular exterior portion 6, the inside diameter of which corresponds to the outside diameter of the housing 2 such that the portion 6 can glide on the outside of the external surface 7 of the housing 2, and an interior tubular portion 8, the outside diameter of which corresponds to the inside diameter of the housing such that the portion 8 can glide on the internal surface 9 of the housing 2. The exterior slide portion 6 is through a longitudinal groove 10 in the wall 11 of the housing connected with the interior slide portion 8 by means of a feather key 12 which is pressed into a slot 13 in the interior slide portion 8 and is in engagement with an elongated hole 14 in the exterior slide portion 6. If the housing 2 and the exterior slide portion 6 are made of metal, such as e.g. aluminium, and the interior slide portion 8 is made of a softer material, such as e.g. plastic, the feather key 12 can advantageously be in flexible engagement with the two slide portions 6, 8, such that the exterior portion 6 guides the movement of the syringe holder 5 itself at injection, and that the interior portion 8 is essentially self-guiding.

Vice versa, the feather key 12 can connect the slide portions 6, 8 in a rigid manner, whereby the interior slide portion 8 can entirely or in part control the movement of the syringe holder 5, dependent on the tolerances of the faces of the slide portions in contact with the housing 2. The slide portions 6, 8 do not need to be in contact with the housing 2 along the entire circumference, e.g. the exterior portion 6 can on its inner side have longitudinal ribs which are in contact with the housing 2 or a portion of its wall can be omitted such that it merely encircles the housing partially. The slide 3 has on the outside two opposite depressions 75 for guiding back the slide with the finger tips, cf. FIGS. 8 and 9.

The syringe holder 5 has a rib 15 with a dovetailed cross section where the rib 15 can be inserted in an adequate key slot 16 in the exterior slide portion 6, cf. FIG. 7. The elongated hole 14 for the feather key 12 being formed in the bottom of the key slot 16, the feather key 12 can be kept in place by the syringe holder 5, but it may also e.g. be fastened by gluing. When the rib 15 is inserted entirely in the key groove 16, a stop 17 at one end of the rib 15 abuts on two bevels 18 in the walls of the key slot, and at the same time, a resilient bow 19 at the other end of the rib 15 hooks down on an end border 20 of the key slot 16. In this way, the syringe holder 5 is locked on the slide portion 6, and by lifting the bow 19, the syringe holder 5 can be replaced. Other locking mechanisms than the stop 17 and the bow 19 are possible. Different syringe holders 5 can thus be mounted dependent on the form of the hypodermic syringe 4 to be used. The shown syringe holder 5 has clamps 76 which can resiliently seize the hypodermic syringe 4, as appears from FIGS. 5 and 6, however, other holding devices are possible.

The interior slide portion 8 has a coaxial bore which is composed of a top section 27 and a bottom section 28, where the top section 27 has a larger diameter than the bottom section 28. In the bottom bore section, a bush in the form of a tube section 21 is pressed in and extends from the lower edge of the slide portion 8 to a little above the upper edge of said portion and encircles a release tube 22 which is fixedly mounted centrally in the housing 2. A lower end of the release tube 22 is inserted in a blind hole 23 in an intermediate plug 24 which is pressed into the lower part of the housing 2, and an upper end of the release tube 22 is inserted in an intermediate hole section 26 in a plug 25 which is screwed in the upper end of the housing 2.

A compression spring 29 is at its lower end inserted in the annular hole between the tube section 21 and the wall of the bore section 27 in the slide portion 8 and at its upper end inserted in a lower hole section 30 which in the plug 25 is designed coaxially under the intermediate section 26 and with a larger diameter than the latter. Extending in the bores 27, 30 in the slide portion 8 and the plug 25, respectively, the spring 29 can, when compressed, be completely received herein such that the slide portion 8 can be guided to a retracted position, where the upper edge of the slide portion 8 is situated immediately below the plug 25.

In the release tube 22, a release rod 31 is guided coaxially with its lower end pretensioned upward by means of a compression spring 32 abutting towards the bottom on a plug 33 inserted in the lower end of the release tube 22. The upper end of the rod 31 is embedded in a release button 34 projecting axially from the housing 2, the button being kept in place towards the top by means of a retaining ring 35 which is screwed on the plug 25. Approximately in the middle of the release rod 31, a recess is arranged in the form of a diametrically through-going groove 36 which is limited by bevels 37, 38 towards the top and the bottom, respectively. In the groove 36, a pawl 39 is journalled pivotally about a tenon 40 pressed into bores 41 in the wall of the rod 31. The pawl 39 has a first leg 42 which can be swung out through a longitudinal slit 43 in the release tube 22, and a second leg 44 which is loaded by a spring 45 such that the first leg 42 of the pawl is pressed out against the wall of the release tube. The release rod 31 cannot rotate in the release tube 22 since a pin 46 through the upper end of the rod 31 is guided in a longitudinal groove 47 in the wall of the release tube 22, and thus is assured that the first leg 42 of the pawl 39 can be swung out through the slit 43 in the release tube when the leg 42 is situated opposite the slit 43. The spring 45 is a piece of resilient thread, one end of which abuts on the second leg 44 of the pawl 39 and the other end of which abuts on the bevel 38 in the groove 36 and which in the middle is wound around a pin 48 through the wall of the rod 36.

The release rod 31 is in its rest position pressed upward by the spring 32 such that the pawl 39 is opposite the slit 43 in the release tube, and the first leg 42 is thus pressed out through the slit 43, cf. FIG. 1. If the slide 3 is in the lower position shown in FIG. 1, the leg 42 projects out through the slit 43, but when displacing the slide 3 to the retracted position shown in FIG. 2, the pawl leg 42 can be swung in through the slit 43 by passage of the bush 28 in the slide portion 8. When the slide 3 is in the retracted position, the pawl leg 42 is again swung out through the slit 43, and the lower edge of the bush 28 abuts on the pawl leg 42 such that the slide 3 is retained in the retracted position where the spring 29 is compressed. If the release button 34 is then activated, the release rod 31 is displaced downward in the release tube 22 whereby the pawl 39 is displaced downward in relation to the slit 43. The pawl leg 42 thus hits a lower edge 49 of the slit 43 and is swung into the release tube 22 such that the bush 28 in the slide portion 8 can pass the pawl 39, and thus the slide 3 is displaced fast downward to the injection position influenced by the spring 29. In the FIG. 3, the slide 3 is displaced to the injection position, and the release button 34 is still pushed down. A rubber ring 50 arranged above the plug 24 softens the impact of the slide portion 8 on the plug 24. Furthermore, the impact is softened by creating an air pressure in the housing 2 between the plug 24 and the slide portion 8.

In order to prevent an unintentional release of the slide 3 from its retracted position, the injection device 1 is provided with a locking mechanism which can be operated by turning a lock ring 51 in the form of a tube section which is journalled around the plug 25 between the housing 2 and the retain ring 35. The lock ring 51 is knurled on the outside for better seizure by the finger tips. In the plug 25 opposite the lock ring 51 around the rod 31, a cavity 52 is surrounded by a cylindrical wall 53 of the plug 25. A lever 54 has a first end 55 which is embedded in a hole 56 in the plug wall 53 such that the lever 54 can tilt in the hole 56 by displacement in the cross direction of the tubular housing 2, cf. FIG. 4. A second end 57 of the lever 54 can at the displacement be moved in a slit 58 extending in the circumferential direction of the cylindrical wall 53. The other end 57 of the lever is moreover in engagement with a depression 59 in the inside of the lock ring 51 such that the lever 54 can be tilted by turning the lock ring 51. The lever 54 is by means of a torsion spring 60 pretensioned such that the middle section of the lever engages a circular groove 61 in the rod 31 when the rod is in its inactivated rest position. The threads of the torsion spring 60 are extending round along the inside of the plug wall 53, its one end is embedded in a hole 62 in the plug wall, and its second end abuts on the second end 57 of the lever 54.

When the slide 3 is in its retracted position, the release rod 31 can only be displaced away from its rest position for release of the slide by first turning the lock ring 51 such that the lever 54 is brought out of engagement with the groove 61 and then keeping the lock ring in this position and at the same time pressing the release button 34 downward. An unintentional release is thus prevented, also in the case where the lock ring has been turned once and then released, and where the release of the slide was not effected anyhow, as the lock ring automatically turns back when released.

The injection device 1 can moreover be provided with a not shown seize device which can seize the piston of the hypodermic syringe at injection when moving the slide 3 from the retracted position to the injection position such that the piston is pulled a little backward in the syringe. An underpressure can thus be created in the syringe such that when inserting the needle in a vein, blood will be drawn into the hypodermic syringe. If this happens, the syringe can be retracted and a new injection in another skin area can be made. The seize device can e.g. be designed as a resilient bow mounted on the housing 2.

In the lower end of the housing 2, there is arranged a tubular lamphouse 63 which through a longitudinal slit 64 in the wall of the housing 2 is connected integrally with a tube section 65 extending next to and parallel to the housing 2 and the lower end of which piece constitutes a bow which can be pressed against a skin area where an injection is to be made. The upper edge of the tube section 65 is cut obliquely upward in the direction of the housing 2 such that the lower part of a hypodermic syringe 4 will be visible in the injection position of the slide 3. Furthermore, the lamphouse 63 is made integrally with the tube section 65 of limpid plastic such that light from a lamp 66 mounted in the lamphouse 63 can illuminate both the syringe and the skin area.

The lamp 66 is arranged in the lamphouse 63 at the connection through the slit 64 to the tube section 65, the legs of the lamp being welded on either side of a printed board 67 which is retained in a plug 68 inserted in the upper end of the lamp holder 63 and upon which connections are provided to the upper ends of two springs 69, 70 arranged concentrically and coaxially in the lamp holder. The lower end of the outer spring 70 is in contact with the outer circular pole of a cylindrical electric cell 71, and the lower end of the inner spring 69 can be brought into contact with the central pole of the cell 71 by displacement of the cell axially upward in the lamp holder 63. The lower end of the cell 71 is in contact with a push button 72, the lower end of which projects axially out of the device 1 such that the cell 71 can be displaced to light the lamp 66 by pushing the injection device downward against a skin area whereby the button 72 is pressed upward. The button 72 has a soft rubber pad 73 on the underside and is kept in place by a ring 74 screwed on the housing 2. In FIGS. 1, 2 and 5 the lamp is thus not lit, whereas it is lit in FIGS. 3 and 6.

What is claimed is:

1. An injection device (1) with a slide (3) which can be displaced in relation to a housing (2) from a retracted position to an injection position, where the slide (3) comprises a portion (8) situated within the housing (2) and a portion (6) situated outside the housing, both portions (6, 8) being interconnected through a groove (10) in the housing (2), where the portion (6) situated outside the housing (2) has a syringe holder (5) for securing of a hypodermic syringe (4), and where the slide (3) is pretensioned toward the injection position by a spring (29) situated in the housing (2), characterized in that the housing (2) at the groove (10) is constituted by a tube part, the outer and/or inner surface (7, 9) of which forms a guide for the slide (3), and that the slide (3) has one or more contact faces contacting the outer surface, the contacting being distributed over more than half of the circumference of the tube part.

2. An injection device (1) according to claim 1, characterized in that the slide portion (6) situated outside the housing (2) encircles the tube part along the entire circumference of the tube part.

3. An injection device (1) according to claim 2, characterized in that the outside diameter of the tube part is at least 8 mm, and that as a consequence of additional thickness of material, the total weight of the device (1) is at least 40 g.

4. An injection device (1) according to claim 1, characterized in that an elongated release mechanism extends coaxially with the tube part in the housing (2) and carries a pawl (39) which is spring-loaded to engage with and retain the slide (3) in the retracted position of the slide, that the release mechanism can at a first end of the housing (2) cooperate with a release button (34) such that when actuating the release button (34), the pawl (39) can be disengaged from the slide (3), and that the pretensioning spring (29) of the slide is arranged around the release mechanism.

5. An injection device (1) according to claim 4, characterized in that the portion (8) of the slide (3) situated within the housing (2) encircles the release mechanism.

6. An injection device (1) according to claim 4, characterized in that the release mechanism is provided with a locking mechanism which is spring loaded for locking the pawl (39) in the engagement position of the pawl with the slide (3) and which can release the pawl (39) for releasing by operation of a lock button (51).

7. An injection device (1) according to claim 1, characterized in that the housing (2) has at its other end a lamp (66) which can be lit by actuation of an axially projecting push button (72).

8. An injection device (1) according to claim 1, characterized in that the housing (2) has at its other end a bow (65) which can be pressed against and extend a skin surface where an injection is to be made, and that the bow (65) is made of a light transmitting material and can be illuminated by a lamp (66).

9. An injection device (1) according to claim 1, characterized in that the outside diameter of the tube part is at least 12 mm, and that as a consequence of additional thickness of material, the total weight of the device (1) is at least 60 g.

10. An injection device (1) according to claim 5, characterized in that the portion (8) of the slide (3) situated within the housing (2) close a cavity between the release mechanism and the internal surface of the tube part.

11. An injection device (1) with a slide (3) which can be displaced in relation to a housing (2) from a retracted position to an injection position, where the slide (3) comprises a portion (8) situated within the housing (2) and a portion (6) situated outside the housing, both portions (6, 8) being interconnected through a groove (10) in the housing (2), where the portion (6) situated outside the housing (2) has a syringe holder (5) for securing of a hypodermic syringe (4), and where the slide (3) is pretensioned toward the injection position by a spring (29) situated in the housing (2), characterized in that the housing (2) at the groove (10) is constituted by a tube part, the outer and/or inner surface (7, 9) of which forms a guide for the slide (3), and that the slide (3) has one or more contact faces contacting the guide, the contacting being distributed over more than half of the circumference of the tube part, characterized in that an elongated release mechanism extends coaxially with the tube part in the housing (2) and carries a pawl (39) which is spring-loaded to engage with and retain the slide (3) in the retracted position of the slide, that the release mechanism can at a first end of the housing (2) cooperate with a release button (34) such that when actuating the release button (34), the pawl (39) can be disengaged from the slide (3), and that the pretensioning spring (29) of the slide is arranged around the release mechanism, and characterized in that the release mechanism comprises a release tube (22) with a rod (31) which can be displaced axially in the tube, and that the pawl (39) is pivotally journalled in a recess (36) in the rod (31) and has an end (42) which can project through a slit (43) in the release tube (22), and which at displacement of the rod (31) can be swung into the tube (22).

12. An injection device (1) with a slide (3) which can be displaced in relation to a housing (2) from a retracted position to an injection position, where the slide (3) comprises a portion (8) situated within the housing (2) and a portion (6) situated outside the housing, both portions (6, 8) being interconnected through a groove (10) in the housing (2), where the portion (6) situated outside the housing (2) has a syringe holder (5) for securing of a hypodermic syringe (4), and where the slide (3) is pretensioned toward the injection position by a spring (29) situated in the housing (2), characterized in that the housing (2) at the groove (10) is constituted by a tube part, the outer and/or inner surface (7, 9) of which forms a guide for the slide (3), and that the slide (3) has one or more contact faces contacting the guide, the contacting being distributed over more than half of the circumference of the tube part, characterized in that an elongated release mechanism extends coaxially with the tube part in the housing (2) and carries a pawl (39) which is spring-loaded to engage with and retain the slide (3) in the retracted position of the slide, that the release mechanism can at a first end of the housing (2) cooperate with a release button (34) such that when actuating the release button (34), the pawl (39) can be disengaged from the slide (3), and that the pretensioning spring (29) of the slide is arranged around the release mechanism, characterized in that the release mechanism is provided with a locking mechanism which is spring loaded for locking the pawl (39) in the engagement position of the pawl with the slide (3) and which can release the pawl (39) for releasing by operation of a lock button (51), and characterized in that a rod (31) of the release mechanism has a circular groove (61) with which a lever (54) can engage when the rod (31) is in its inactivated position where the pawl (39) can engage with the slide (3), that the lock button is designed as a lock ring (51) which when turned coaxially about the rod (31) can lift the lever (54) out of engagement with the groove (61), and that the lock ring (51) is situated at the release button (34).

13. An injection device (1) with a slide (3) which can be displaced in relation to a housing (2) from a retracted position to an injection position, where the slide (3) comprises a portion (8) situated within the housing (2) and a portion (6) situated outside the housing, both portions (6, 8) being interconnected through a groove (10) in the housing (2), where the portion (6) situated outside the housing (2) has a syringe holder (5) for securing of a hypodermic syringe (4), and where the slide (3) is pretensioned toward the injection position by a spring (29) situated in the housing (2), characterized in that the housing (2) at the groove (10) is constituted by a tube part, the outer and/or inner surface (7, 9) of which forms a guide for the slide (3), and that the slide (3) has one or more contact faces contacting the guide, the contacting being distributed over more than half of the circumference of the tube part, characterized in that the syringe holder (5) is detachably fastened on the slide (3), and that it can be fastened by insertion in a key slot (16) where it is retained by a resilient bow (19) in engagement with the slide (3).

* * * * *